US006929678B2

(12) United States Patent  Hartlein

(10) Patent No.: US 6,929,678 B2
(45) Date of Patent: Aug. 16, 2005

(54) PURGE AND TRAP CONCENTRATOR WITH IMPROVED DRYING

(75) Inventor: Thomas M. Hartlein, Lebanon, OH (US)

(73) Assignee: Teledyne Tekmar Company, Mason, OH (US)

( * ) Notice: Subject to any disclaimer, the term of this patent is extended or adjusted under 35 U.S.C. 154(b) by 47 days.

(21) Appl. No.: 10/440,661

(22) Filed: May 19, 2003

(65) Prior Publication Data

US 2004/0231509 A1 Nov. 25, 2004

(51) Int. Cl.$^7$ .......................... B01D 15/08; B01D 53/04; B01D 53/26
(52) U.S. Cl. ................... 95/18; 95/87; 95/126; 96/102; 96/105; 96/112; 96/118
(58) Field of Search ................... 95/17, 18, 82, 95/87, 89–91, 117, 123, 125, 126; 96/101, 103, 104, 105, 112, 118, 143, 146, 154

(56) References Cited

U.S. PATENT DOCUMENTS

| 4,915,715 A | * | 4/1990 | Oshima et al. ............... 96/118 |
| 5,497,561 A | * | 3/1996 | Murray et al. ................. 34/80 |
| 5,616,158 A | * | 4/1997 | Biendarra et al. .......... 96/117.5 |
| 6,223,584 B1 | * | 5/2001 | Mustacich et al. .......... 73/23.41 |
| 6,358,300 B1 | | 3/2002 | Fornof et al. .................. 95/91 |
| 6,423,120 B1 | * | 7/2002 | Nickerson et al. ............. 95/87 |
| 6,541,272 B1 | * | 4/2003 | Mitra ......................... 436/178 |
| 6,656,738 B1 | * | 12/2003 | Vogel et al. ................. 436/161 |

OTHER PUBLICATIONS

Web page entitled "SKC Thermal Desorption Tubes," dated Mar. 30, 2002, SKC Corporate Headquarters in the USA; pp. 1–5.

* cited by examiner

Primary Examiner—Robert H. Spitzer
(74) Attorney, Agent, or Firm—Kirkpatrick & Lockhart; Nicholson Graham LLP

(57) ABSTRACT

A purge and trap concentrator and a method for drying a stream of sample gas in a gas analysis instrument. A dryer tube has an inlet that receives a stream of sample gas during a drying interval and receives a stream of dry gas during a regeneration interval. The dryer tube also has an outlet and an interior passageway between the inlet and an outlet. Support material comprising polymer sorbent is placed in the interior passageway and provides a support surface area for a hygroscopic coating comprising lithium chloride. A controller controls a heater to increase the temperature of the dryer tube to between 100 and 300 degrees centigrade during the regeneration interval and controls the heater to decrease the temperature of the dryer tube to below 100 degrees centigrade during the drying interval.

17 Claims, 8 Drawing Sheets

US 6,929,678 B2

PURGE AND TRAP CONCENTRATOR WITH IMPROVED DRYING

FIELD OF THE INVENTION

The present invention relates generally to purge and trap concentrators. More specifically, the invention relates to hygroscopic dryers for such instruments.

BACKGROUND OF THE INVENTION

A purge and trap concentrator, such as the Tekmar-Dohrmann 3100 Sample Concentrator, receives a liquid sample that typically includes volatile compounds. When the purge and trap concentrator heats the liquid sample and passes a purge gas through it, volatile compounds are purged from the liquid as gas or vapor and are trapped in a trap. The trapped volatile compounds are then transferred to a gas chromatograph or other chemical analysis instrument for chemical analysis. There is a need to consistently dry the volatile compounds before they are transferred to the chemical analysis instrument. A lithium chloride dryer is typically used for drying the transferred volatile compounds.

In purge and trap applications, the lifetime of a dryer using lithium chloride is limited. The dryer is cycled repeatedly to absorb water, and then the dryer is baked to remove moisture before the dryer is returned to service in the purge and trap concentrator.

The lithium chloride is an inorganic salt that is very hygroscopic. Lithium chloride efficiently scavenges moisture from sample gas with which it comes in contact. When used alone, however, lithium chloride, tends to solidify or cake up as it accumulates water. The surface area of the lithium chloride is reduced with repeated use and baking. Eventually, lithium chloride tends to solidify so much that it blocks flow of the sample gas, and the efficiency of moisture removal is greatly reduced.

A purge and trap concentrator and method are needed that will extend the useful lifetime of lithium chloride for drying a stream of sample gas in a purge and trap concentrator.

SUMMARY OF THE INVENTION

Disclosed are a purge and trap concentrator and a method for drying a stream of sample gas in a purge and trap concentrator. A dryer tube in the purge and trap concentrator has an inlet that receives a stream of sample gas during a drying interval and receives a stream of dry gas during a regeneration interval. The dryer tube also has an outlet and an interior passageway between the inlet and an outlet.

Support material comprising polymer sorbent is placed in the interior passageway and provides a support surface area for receiving a hygroscopic coating. The hygroscopic coating comprises lithium chloride.

A controller controls a dry gas metering system to provide a regulated flow of dry gas through the interior passageway during the regeneration interval. A heater heats the lithium chloride and to increase its temperature to between 100 and 300 degrees centigrade during the regeneration interval and controls the heater to decrease the temperature to below 100 degrees centigrade during the drying interval.

These and various other features as well as advantages that characterize the present invention will be apparent upon reading of the following detailed description and review of the associated drawings.

DETAILED DESCRIPTION OF ILLUSTRATIVE EMBODIMENTS

In the embodiments illustrated below, a dryer tube containing lithium chloride deposited on polymer sorbent is placed in a temperature programmable device that includes a heater and preferably also includes a fan. This dryer tube is placed in line with a dry gas metering system such as a mass flow controller. The temperature of the dryer tube is elevated to a set point between 100 and 300 degrees Celsius. Once the desired set point is reached the dry gas metering system is programmed to deliver a flow rate between 200 and 500 milliliters per minute of a dry gas. This flow is then directed through the dryer tube to an atmospheric vent. As the dryer tube is heated, moisture is released from the lithium chloride and carried away by the incoming gas to the vent. The dryer tube is thus regenerated. After a programmed time, preferably between 1 and 10 minutes, the temperature programmable device and the dry gas metering system are returned to their moisture removal set points and the lithium chloride is prepared for further water removal from samples produced by the purge and trap concentrator.

In the embodiments illustrated below, the lifetime of a dryer using lithium chloride in a purge and trap concentrator is extended by placing a coating that includes lithium chloride in a thin layer on a support layer that includes polymer sorbent. The dryer can be used repeatedly to absorb water and then can be regenerated by heating without loss of efficiency or blockage of gas flow. The thin layer of lithium chloride efficiently scavenges moisture from a stream of sample gas. The lithium chloride maintains a large surface area in contact with the flow of sample gas and maintains its efficiency is spite of further solidification or "caking up" as it accumulates water. The polymer sorbent extends the useful lifetime of lithium chloride for drying a stream of sample gas in a gas analysis instrument.

Figure 1:
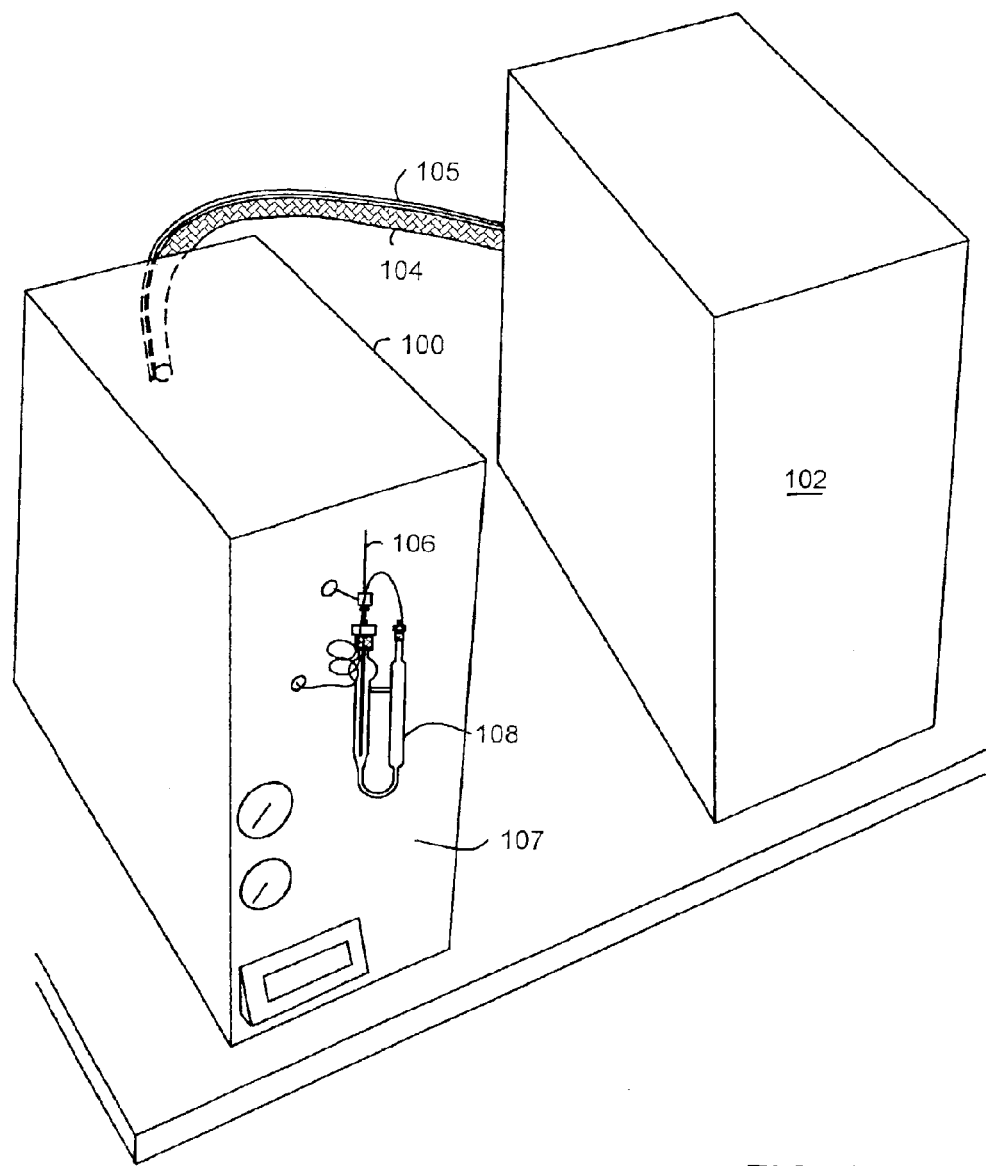
FIG. 1 illustrates a first embodiment of a purge and trap concentrator connected to a gas analysis instrument.

FIG. 1 illustrates a first embodiment of a purge and trap concentrator 100 connected to a gas analysis instrument 102 by a heated outlet line 104. The gas analysis instrument is typically a gas chromatograph, however other gas analysis instruments can be used. A carrier gas line 105 is secured to an outer sheath of the heated outlet line 104 and couples from the gas analysis instrument 102 to the purge and trap concentrator 100. The purge and trap concentrator 100 performs purge and trap functions on chemical samples. The purge and trap concentrator has a sample inlet 106.

Typically, a chemical sample is injected at inlet 106 using a syringe (not illustrated). The injected chemical sample is received in a sparging tube 108 that is part of the purge and trap concentrator 100, but is mounted externally on front panel 107 for easy access. The chemical sample is processed in the purge and trap concentrator 100 and then a concentrated chemical sample is coupled via the heated outlet line 104 to the gas analysis instrument 102. A digital controller in the purge and trap concentrator 100 completes a system cycle of sequential steps or modes that typically include a purge mode, a dry purge mode, a desorb preheat mode, a desorb mode, a bake mode and a trap cooldown mode. Upon completion of the trap cooldown mode, the purge and trap concentrator is ready to begin another system cycle with the next sample. During the desorb mode, the purge and trap concentrator delivers a sample that is passed through a lithium chloride dryer to remove moisture before the sample is passed on to the chemical analysis instrument 102. An example of the various flow paths in the purge and trap concentrator 100 are described in more detail below in connection with FIGS. 2–3. An example of a controller that controls the sequential modes in the cycle of the purge and trap concentrator 100 is also described in more detail below in connection with FIG. 4.

Figure 2:
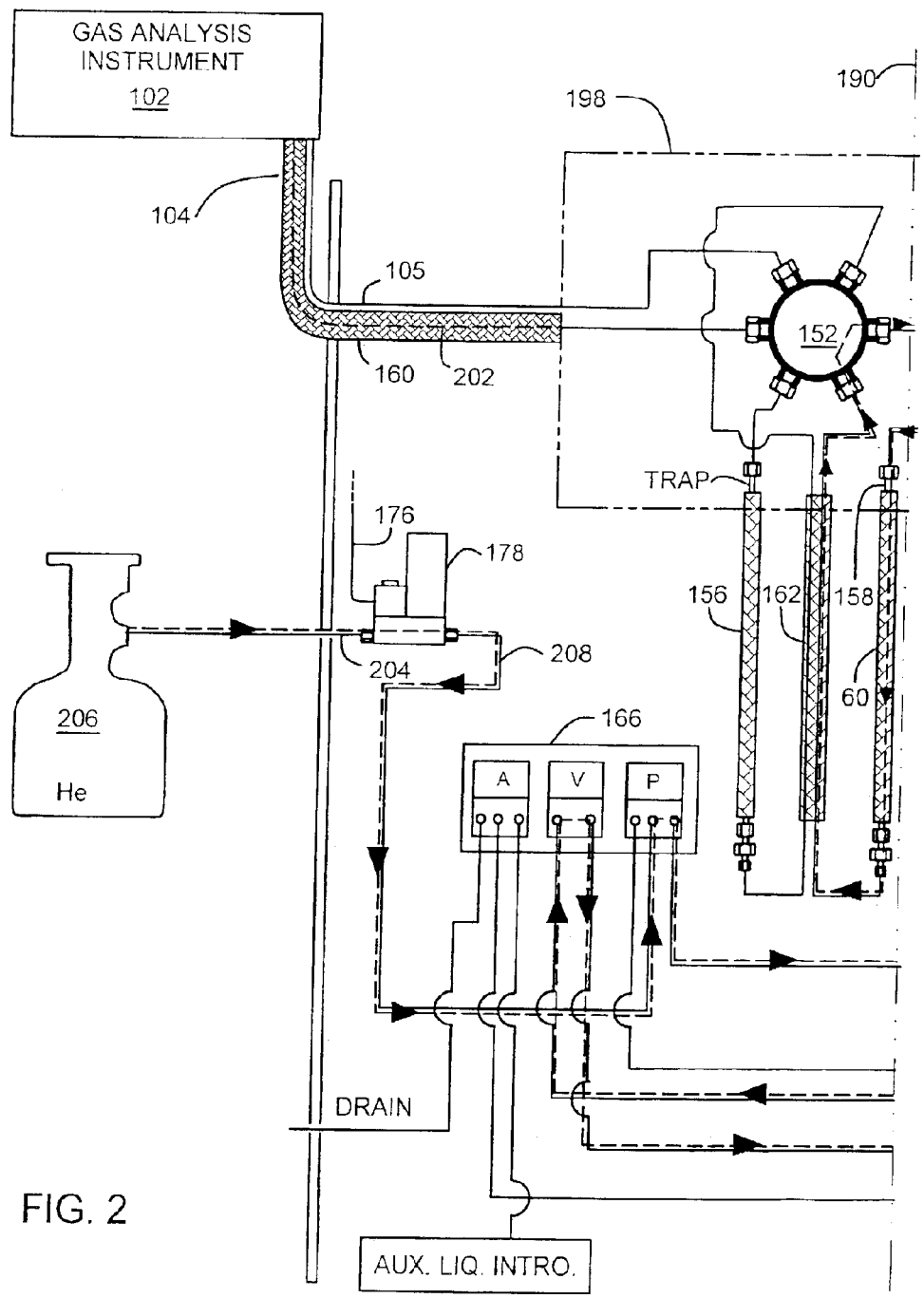
FIGS. 2–3, taken together, schematically illustrate fluid handling in a purge and trap concentrator connected to a gas analysis instrument.
Figure 3:
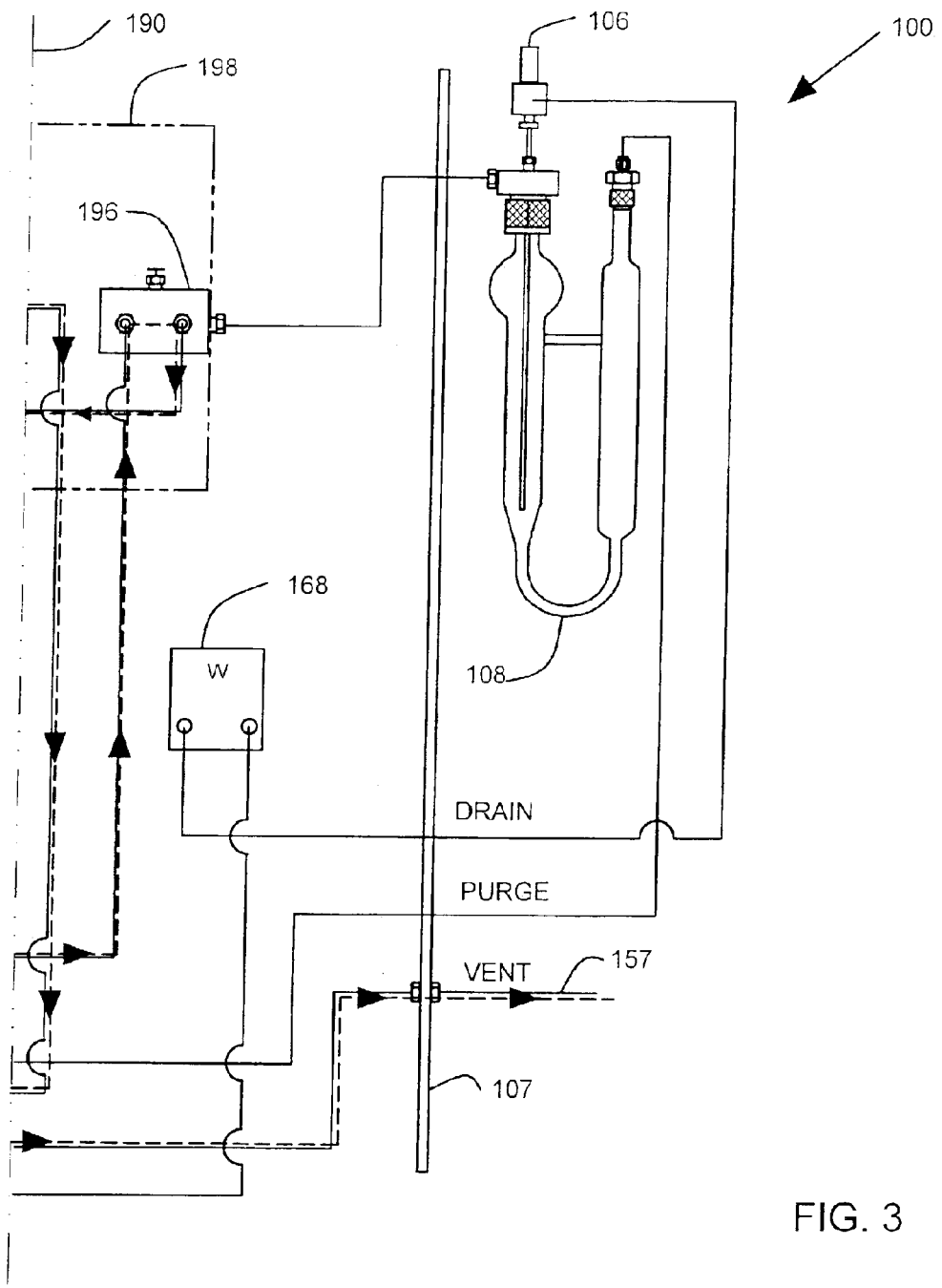

FIGS. 2–3, taken together, schematically illustrate a block diagram of fluid handling in an exemplary purge and trap concentrator connected to a gas analysis instrument 102. For convenience in reading FIGS. 2–3, the right edge of FIG. 2 can be joined with the left edge of FIG. 3 along broken line 190 in each of FIGS. 2–3. Reference numbers used in FIGS. 2–3 that are the same as reference numbers used in FIG. 1 identify the same or similar features.

In this embodiment, the purge and trap concentrator 100 includes a plurality of fluid control devices such as 6 port valve 152, valve manifold 166, four way tee valve 168 and heated sparging tube 108. A network of fluid passageways (illustrated by solid lines) interconnect the fluid control devices 152, 166, 168 and 108. Some of the interconnecting lines and other devices are heated as indicated by heater jackets with a herringbone pattern in FIGS. 2–3. The 6 port valve 152 and a four way tee valve 196 are placed in a heated valve oven 198. A sample inlet 106 is arranged to receive a chemical sample. A sample outlet 202 (inside an outlet line heater 160) is arranged to provide a concentrated chemical sample to the gas analysis instrument 102.

A purge gas inlet 204 is arranged to receive dry purge gas from a gas bottle 206 that is typically external to the purge and trap concentrator. In a preferred arrangement, a mass flow controller 178 couples to the purge gas inlet 204 and provides an electrically adjustable rate of flow of the purge gas on line 208 to a valve P in the valve manifold 166 in the purge and trap concentrator 100. Other known gas metering systems can be used in place of the mass flow controller 178. The rate of flow of purge gas is adjustable automatically as a function of an electrical input 176 that is provided by the digital controller 154 described below in connection with FIG. 4.

The mass flow controller (MFC) 178 can be a commercially available flow controller, for example, of the type used to control the flow of gases in semiconductor manufacturing processes. The mass flow controller 178 typically includes a mass flow sensor, a valve and a control circuit that receives the electrical input 176 as a set point and controls the valve as a function of a difference between the set point and an ouput from the mass flow sensor. During normal operation of the purge and trap concentrator, the mass flow controller 178 is controlled as needed to provide flow control for purge and trap operations.

During a regeneration interval, the mass flow controller 178 is set to provide a flow of dry purge gas at a rate needed to remove moisture from a dryer tube 158 in the purge and trap concentrator. In one preferred embodiment, the rate of dry purge gas flow is controlled by the mass flow controller 178 to about 200–500 milliliters per minute.

During the regeneration interval, dry purge gas (typically dry helium) is coupled along a dashed line starting at gas bottle 206, passing through the mass flow controller 178 to outlet line 208, passing through valve P in valve manifold 166, then passing through four way tee valve 196, then passing through the dryer tube 158. Passing through the dryer tube 158, the purge gas picks up moisture and continues on through a line heater 162, six port valve 152, valve V of valve manifold 166 and out atmospheric vent 157. Flow control devices in the purge and trap concentrator are controlled by a digital controller 154 as explained below in connection with an example in FIG. 4.

Periodically, an additional regeneration mode is added after completion of a purge and trap cycle in order to regenerate lithium chloride dessicant in the dryer tube 158. During regeneration, dry purge gas passes through the dryer tube 158 at a rate controlled by the mass flow controller and the dryer tube is heated by dryer tube heater 60 to an elevated temperature long enough to drive accumulated moisture out of the dry tube 158. In a preferred arrangement, the regeneration time interval is in the range of 1–10 minutes. Regeneration can be performed automatically based on a fixed time interval of operation, or a selected number of samples processed by the dryer tube 158. Regeneration can also be manually initiated when an operator notices that the gas analyzer 102 indicates that it is receiving excess moisture with the purged sample.

Figure 4:
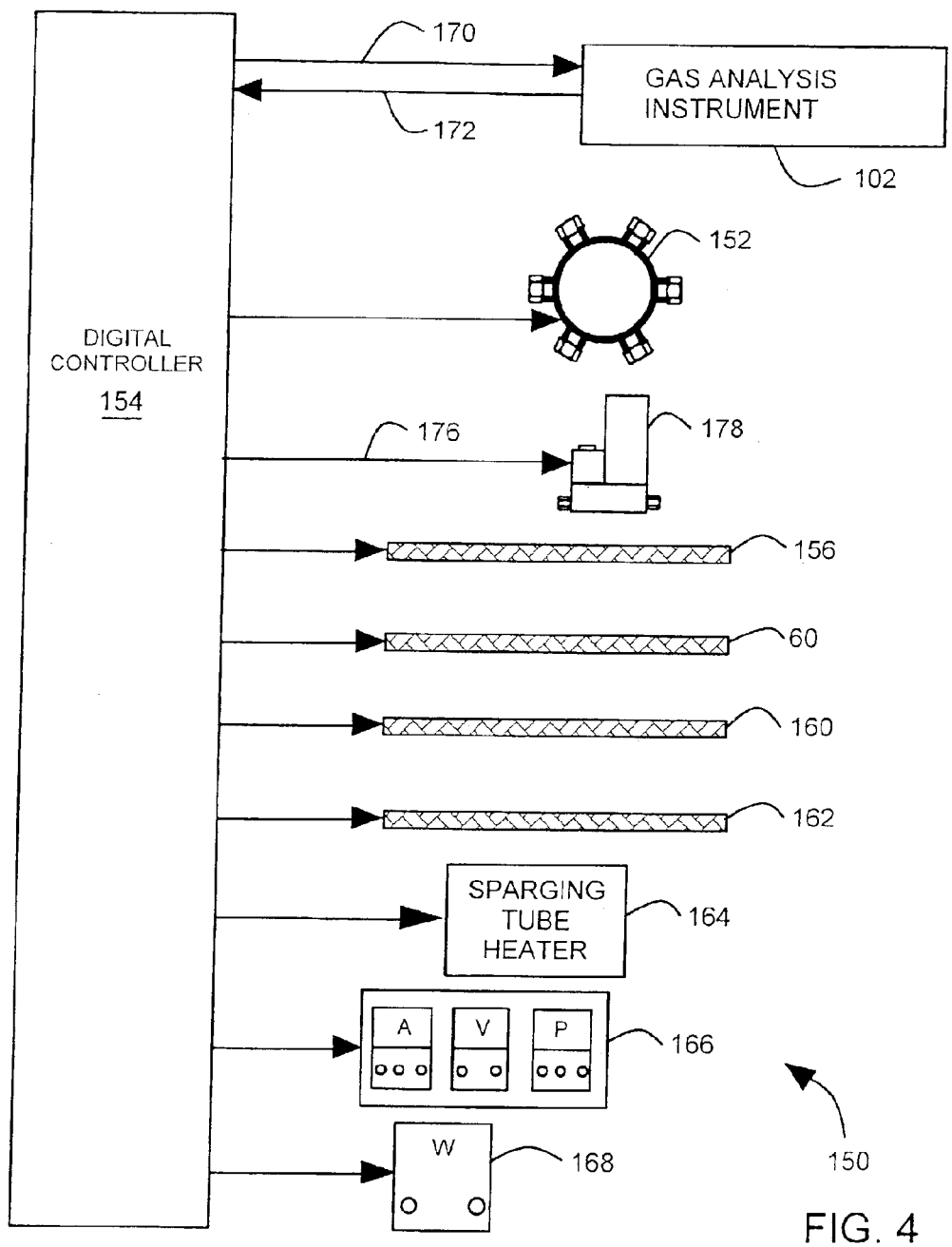
FIG. 4 schematically illustrates a block diagram of electrical connections in a purge and trap concentrator.

FIG. 4 schematically illustrates a block diagram 150 of electrical connections in a purge and trap concentrator such as the one illustrated in FIG. 1. Reference numbers used in FIG. 4 that are the same as reference numbers used in FIGS. 1–3 identify the same or similar features. The digital controller 154 automatically actuates fluid control devices such as the 6 port valve 152, the valve manifold 166 and the drain valve 168. The digital controller 154 also actuates a trap heater 156, the dryer tube heater 60, an outlet line heater 160, a line heater 162, and a sparging tube heater 164. The digital controller 154 can also control other devices (not illustrated) as well, such as the oven 198 for the six port valve 152, a sample mount heater, or a fan. The digital controller 154 can receive data from temperature sensors (not illustrated in FIG. 4) and operator inputs. External connections 170, 172 are provided so that the digital controller 154 can communicate with a gas analysis instrument 102 to synchronize the operation of the purge and trap concentrator 100 with the operation of the gas analysis instrument 102. The digital controller 154 also provides the electrical input 176 to a mass flow controller 178. The mass flow controller 178 adjusts the flow of purge gas as a function of the electrical input 176. The electrical input 176 can be analog or digital and provides an indication to the mass flow controller of a desired flow rate for the purge gas flow.

The digital controller 154 provides a time sequence or system cycle as explained above in connection with FIG. 1 that includes a mode or time interval for regeneration of the dryer tube 158. The digital controller 154 typically comprises a microprocessor system with I/O devices interfacing with the various valves, heaters, the mass flow controller 178 and the gas analysis instrument 174 as well as other optional devices (not illustrated) such as fans, temperature sensors, a keyboard, switches and a display for the operator.

Figure 5:
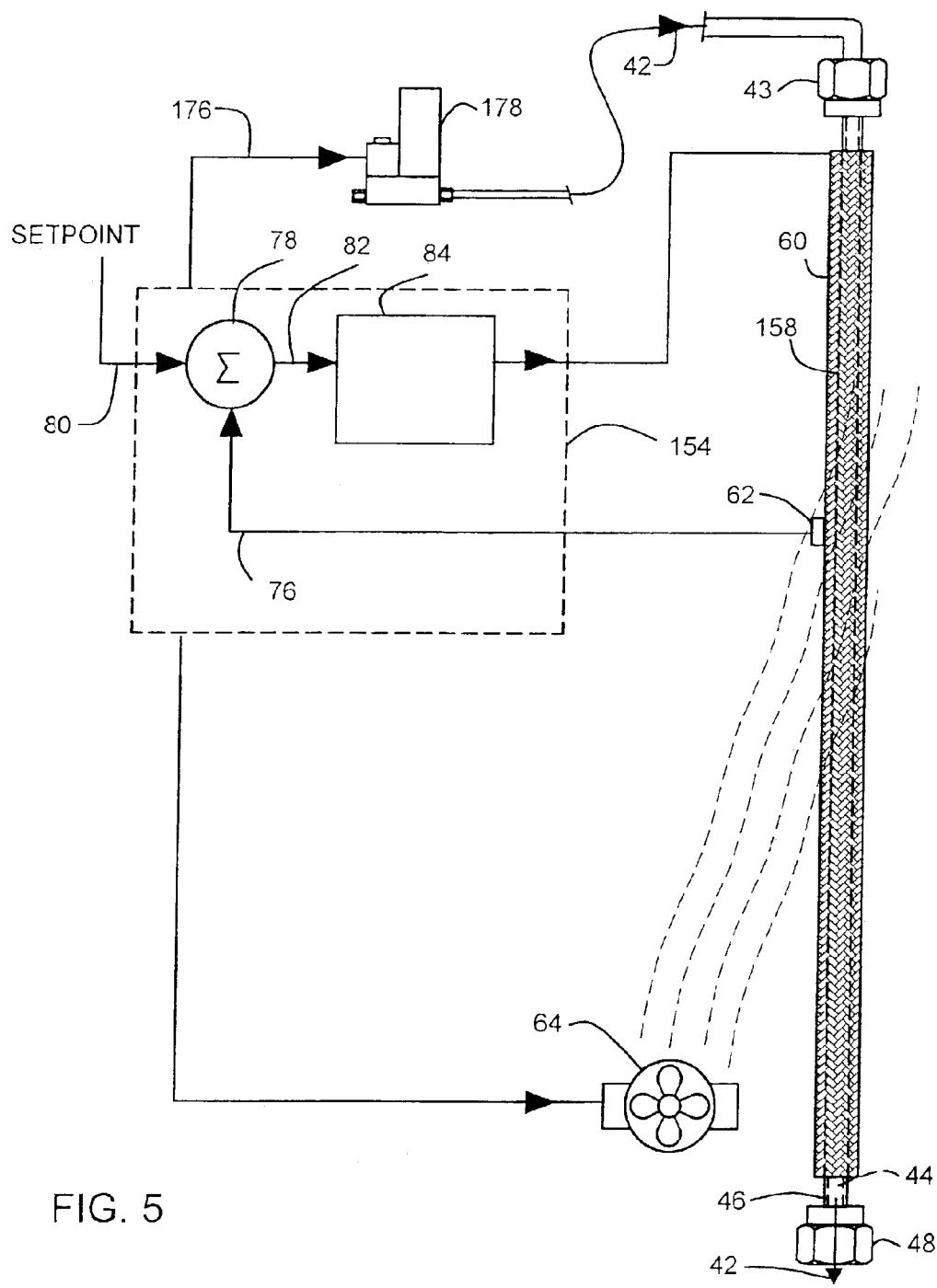
FIG. 5 illustrates a block diagram of a second embodiment of an apparatus for drying a stream of sample gas in a purge and trap concentrator.

FIG. 5 illustrates a block diagram of portions of a second embodiment of a purge and trap concentrator that includes a dryer tube 158 for drying a stream of sample gas. Reference numbers used in FIG. 5 that are the same as reference numbers used in FIGS. 1–4 identify the same or similar features.

A temperature controller 84 in a digital controller 154 controls energization of a dryer tube heater 60 to increase the temperature to between 100 and 300 degrees centigrade during a regeneration interval. The temperature controller 84 controls energization of the dryer tube heater 60 to decrease the temperature to below 100 degrees centigrade during the drying interval that is part of the normal cycle of the purge and trap concentrator. In a preferred arrangement, a temperature sensor 62 is arranged on the dryer tube heater 158 and provides temperature feedback 76 to a summing point 78. The temperature controller 84 connects to the summing point 78 that electronically compares the temperature feedback 76 to a temperature setpoint 80. The summing point 78 provides a difference output 82 to the heater controller 84. The heater controller 84 drives the dryer tube heater 60 as a function of the difference output 82. The setpoint 80 has one level during the drying time interval and another level during the regeneration time interval. Closed loop control of the dryer tube heater 60 and the temperature is maintained during both time intervals.

The purge and trap concentrator illustrated in FIG. 5 has the advantage of a relatively simple arrangement, however, the dryer tube 158 is not available for drying a stream of sample gas during the regeneration time interval.

As described above, the dryer tube 158 is used for drying a sample gas in the purge and trap concentrator. A gas stream passes through an interior passageway 44 in the dryer tube 158. The dryer tube has an inlet 43 that receives a stream of sample gas during a drying interval and that receives a stream of dry gas during a regeneration interval. The dryer tube heater is energized at a higher level during the regeneration interval. In a preferred arrangement, at the end of the regeneration interval, a fan 64 is energized to rapidly cool the dryer tube 158 and the dryer tube heater 60. The purge and trap concentrator provides gas stream 42 that is a dried sample gas during a drying interval and provides gas stream 42 as a drying gas during a regeneration interval. The dryer tube 158 preferably includes an annular tube wall 46 surrounding the interior passageway 44 between the inlet 43 and an outlet 48.

In a preferred embodiment, a support material is disposed in the interior passageway 44. The support material preferably comprises Chromosorb polymer sorbent waw 80/100 mesh and has a support surface area. Chromosorb is a trademark of John Mansville Corp. Depending on the application, other sorbent polymers used in analytical sorption tubes can also be used. A hygroscopic coating is deposited on the support surface area. The hygroscopic coating comprises lithium chloride. The support material and the hygroscopic coating can be arranged in the dryer tube in a variety of ways, for example, as illustrated in FIGS. 6–8.

Figure 6:
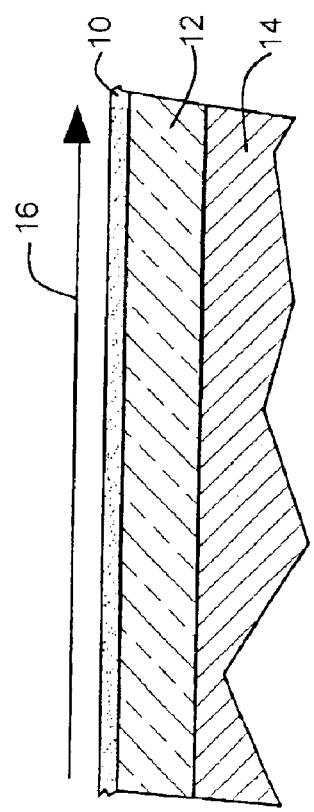
FIG. 6 illustrates a cross-sectional view of a hygroscopic coating on a support surface.

FIG. 6 illustrates a cross-sectional view of a hygroscopic coating 10 comprising lithium chloride on a support layer 12 comprising Chromosorb polymer sorbent waw 80/100 mesh. The support layer 12 is deposited on an interior wall of tubing 14. The tubing 14 has a long length in order to provide a large surface area of the hygroscopic coating 10. A stream of gas 16 flows through the interior passageway over the hygroscopic coating 10. When the hygroscopic coating 10 is heated to a temperature less than 100 degrees Centigrade during a drying interval, then the lithium chloride efficiently scavenges moisture from the gas stream 16. Gas stream 16 is a stream of sample gas that can include moisture during the drying interval. When the hygroscopic coating 10 is heated to a temperature between 100 and 300 degrees Centigrade during a regeneration interval, then the lithium chloride is dried by a flow of dry gas and is regenerated as it releases moisture to the gas stream 16. Gas stream 16 is a stream of dry gas during the regeneration interval.

Figure 7:
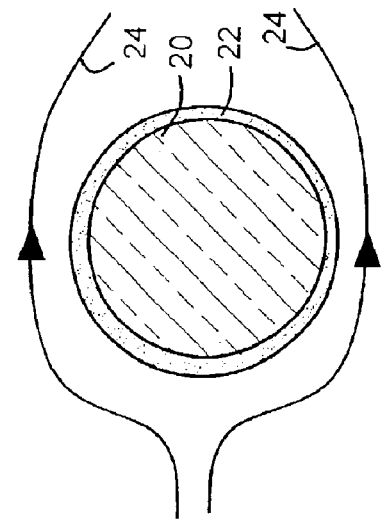
FIG. 7 illustrates a cross sectional view of a fiber with a hygroscopic coating.

Pursuant to another embodiment, FIG. 7 illustrates a cross sectional view of a fiber 20 comprising Chromosorb polymer sorbent with an outer hygroscopic coating 22 comprising lithium chloride. The fiber 20 is disposed inside a dryer tube 158. A gas flow 24 passes over the hygroscopic coating 22, and the hygroscopic coating 22 can absorb water and regenerate as described above in connection with FIG. 6. A large number or long length of fiber can be used to provide a large surface area of hygroscopic coating 22.

Figure 8:
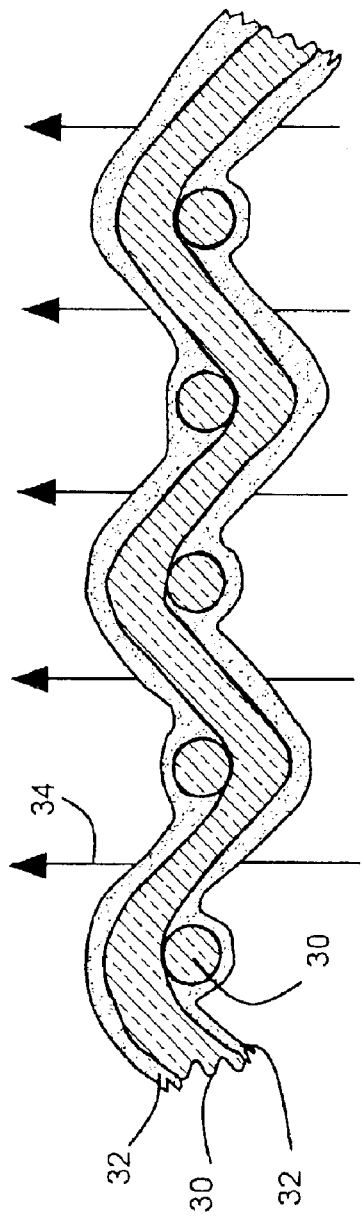
FIG. 8 illustrates a cross-sectional view of a fabric coated with a hygroscopic coating.

In another embodiment, FIG. 8 illustrates a cross-sectional view of a woven support fabric 30 comprising Chromosorb polymer sorbent coated with a hygroscopic coating 32 comprising lithium chloride. The fabric 30 is disposed inside a dryer tube 158. A gas flow 34 passes through opening in the support fabric 30 and contacts the hygroscopic coating 32. The hygroscopic coating 32 can absorb water and regenerate as described above in connection with FIG. 6. The fabric 30 provides a large surface area of hygroscopic layer 32. In a preferred arrangement, the support material can be positioned in the dryer tube by a screen.

In a preferred arrangement, the hygroscopic coatings 10, 22 and 32 have a coating thickness of about 10% of the thickness of the support material. The hygroscopic coatings 10, 22 and 32 can be applied by spraying a mixture of the hygroscopic coating and a solvent on the support surface, and then drying. Alternatively, the support surface can be dipped in a mixture of the hygroscopic coating and a solvent, and then dried.

In FIGS. 6–8, a useful lifetime of a dryer tube 158 using lithium chloride (10, 22 or 32) in a purge and trap concentrator is extended by placing a coating that includes lithium chloride in a thin layer on a support layer that includes Chromosorb polymer sorbent (12, 20 or 30). The dryer tube 158 can be used repeatedly to absorb water and then be regenerated by increased heating without loss of efficiency or blockage of gas flow. The thin layer of lithium chloride efficiently scavenges moisture from a stream of sample gas. The lithium chloride maintains a large surface area in contact with the flow of sample gas and maintains its efficiency in spite of further solidification or "caking up" as it accumulates water.

Figure 9:
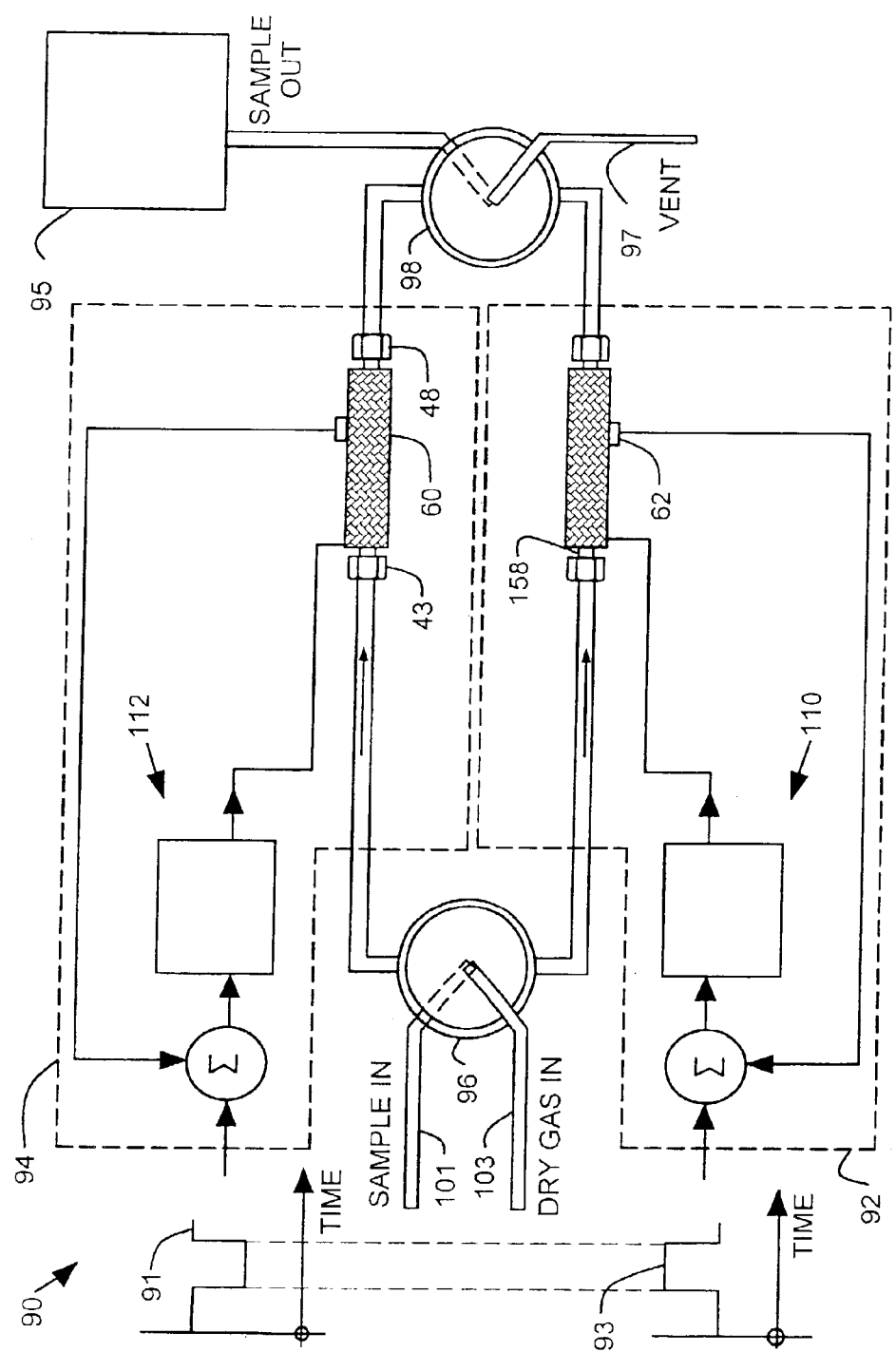
FIG. 9 illustrates a block diagram of a third embodiment of an apparatus for drying a stream of sample gas in a purge and trap concentrator.

In FIG. 9, a dryer arrangement 92 (as described in FIG. 5, for example) and a second apparatus 94 (also as described in FIG. 5, for example) are coupled together by inlet valve 96 and outlet valve 98. The first dryer arrangement 92 operates in a regeneration time interval during the time that the second dryer arrangement 94 operates simultaneously in the drying time interval. After the regeneration time interval of first dryer arrangement 92 is complete, then first dryer arrangement 92 switches to a drying time interval while the second drying arrangement 94 switches to a regeneration time interval. The two dryer arrangements 92, 94 operate out of phase with one another, as illustrated by setpoint waveforms 91, 93, so that one of the dryer arrangements 92, 94 is continuously available for drying a stream of sample gas from the purge and trap concentrator on which it is installed. The analytical instrument can continue to run without waiting for a dryer to regenerate.

The inlet valve 96 couples sample gas from line 101 to apparatus 92 while inlet valve 96 couples dry gas from line 103 to apparatus 94 during a regeneration interval of the apparatus 94. After regeneration of apparatus 94 is complete, then the inlet valve 96 switches position and apparatus 92 is regenerated.

The outlet valve 98 couples dried sample gas from first dryer arrangement 92 to a gas analysis instrument 95 and also couples dry gas (which has picked up moisture) from second dryer arrangement 94 to vent 97 during a regeneration interval of second dryer arrangement 94. After regeneration of second dryer arrangement 94 is complete, then the outlet valves 96, 98 switch position and first dryer arrangement 92 is regenerated while second dryer arrangement 94 provides drying of a stream of sample gas from the purge and trap concentrator.

Each of the drying arrangements 92, 94 includes a temperature controller 110, 112. The temperature controller 110 in the first apparatus 92 provides a drying interval when the temperature controller 112 in the second apparatus is providing a regeneration interval. The purge and trap concentrator provides the stream of sample gas alternatively to first and second inlets in the first and second apparatuses 92, 94 respectively by way of inlet valve 96. The outlets of the first and second dryer arrangements 92, 94 alternately couple to the gas analysis instrument 95. A digital controller (not illustrated in FIG. 9) in the gas analysis instrument controls the operation of valves 96, 98 and provides the setpoint waveforms 91, 93.

The arrangement shown in FIG. 9 and identified by reference numeral 90 is more complex than the arrangement shown in FIG. 5, however, the arrangement in FIG. 9 can be added to an existing purge and trap concentrator without modifying the normal cycle of the existing purge and trap concentrator. The arrangement shown in FIG. 9 can be added on and operate transparently with existing purge and trap concentrator cycles. The arrangement in FIG. 9 also has the advantage that the purge and trap concentrator is continuously "on lines" or available because one dryer tube is being regenerated while the other is in use for drying.

Figure 10:
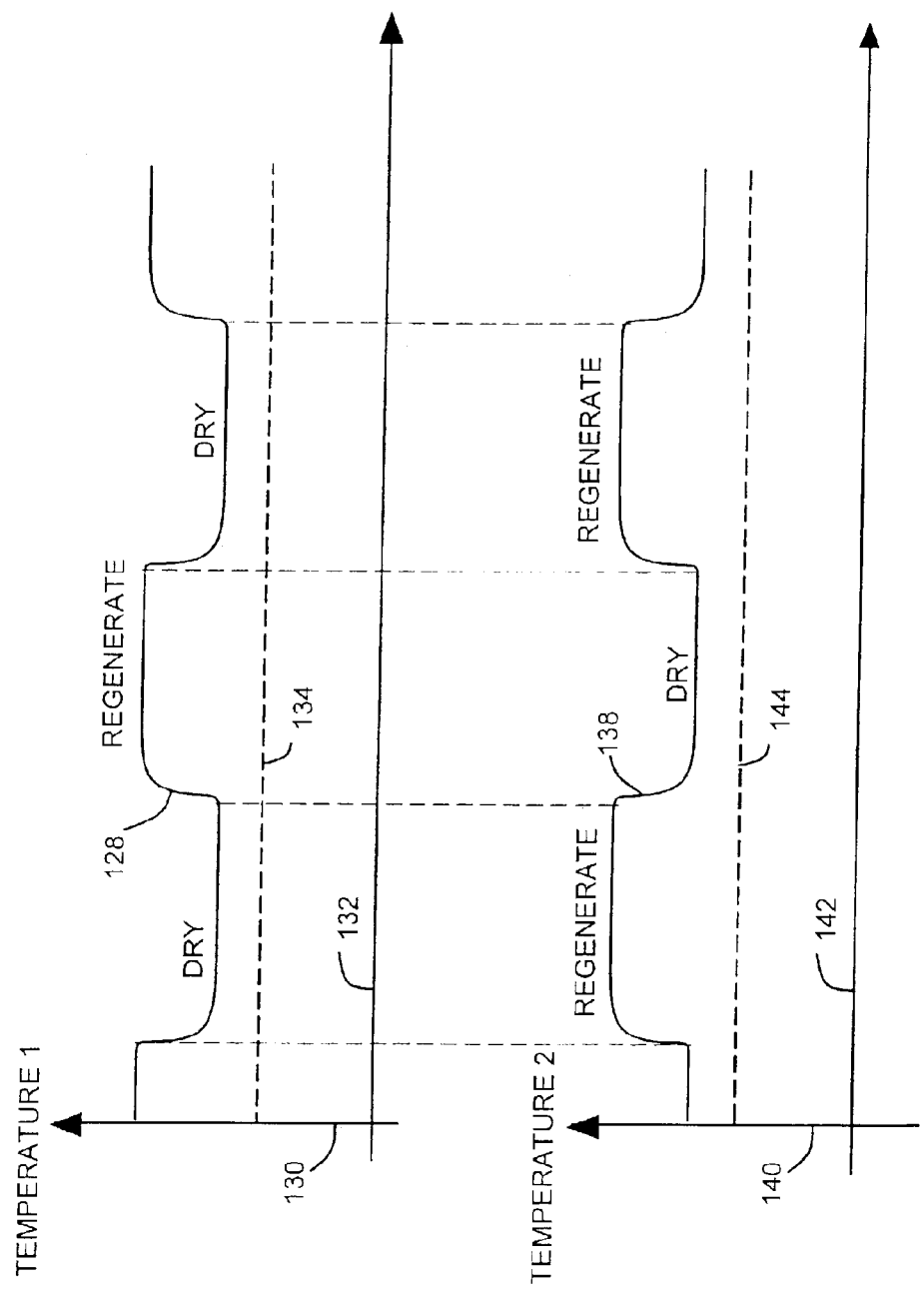
FIG. 10 illustrates an exemplary timing diagram of drying intervals and regeneration intervals in FIG. 9.

FIG. 10 illustrates a timing diagram of temperatures during drying intervals and regeneration intervals in the apparatuses 92, 94 described above in connection with FIG. 9. In FIG. 10, a first vertical axis 130 represents temperature 1 at 128 of the hygroscopic layer in first dryer arrangement 92 and horizontal axis 132 represents a first time axis. A dashed horizontal line 134 represents a temperature below which Chromosorb polymer sorbent absorbs organics from a sample gas stream, and above which it does not absorb organics from a sample gas stream. A second vertical axis 140 represents temperature 2 at 138 of the hygroscopic layer in dryer arrangement 94 and horizontal axis 142 represents a second time axis. A dashed horizontal line 144 represents a temperature below which Chromosorb polymer sorbent absorbs organics from a sample gas stream, and above which it does not absorb organics from a sample gas stream. Temperature 128 is shifted in time relative to temperature 138, and thus one of the dryer arrangements 92, 94 is available for use by the analytical instrument at any given time. The temperatures 128, 138 are maintained above the lines 134, 144 respectively so that the Chromosorb polymer sorbent in the support material does not interfere with the analysis of sample gas.

It is to be understood that even though numerous characteristics and advantages of various embodiments of the invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application for chemical analysis while maintaining substantially the same functionality without departing from the scope and spirit of the present invention. For example, the dryer tube may be a narrow capillary with a coated interior wall or a wider tube with coated support material packed in it. In addition, although the preferred embodiment described herein is directed to a benchtop laboratory style of instrument, it will be appreciated by those skilled in the art that an embodiment as a process analyzer can be implemented as well. The teachings of the present invention can be applied to other chemical processing instruments without departing from the scope of the present invention.

What is claimed is:

1. A method for drying a stream of sample gas in a purge and trap concentrator, comprising:

providing a gas metering system controlling a stream of sample gas during a drying interval and controlling a stream of dry gas during a regeneration interval to a dryer tube, the dryer tube having an inlet and an outlet and an interior passageway between the inlet and an outlet;

placing support material comprising polymer sorbent in the interior passageway, the support material providing a support surface area;

coating the support surface area with a hygroscopic coating comprising lithium chloride, the lithium chloride having a temperature;

heating the dryer tube with a heater, and controlling the heater to increase the temperature of the dryer tube to between 100 and 300 degrees centigrade during the regeneration interval and controlling the heater to decrease the temperature of the dryer tube to below 100 degrees centigrade during the drying interval.

2. The method of claim 1, further comprising:

forming the support material as a fiber.

3. The method of claim 2, further comprising forming a fabric by weaving the fiber.

4. The method of claim 1, further comprising depositing the hygroscopic coating and supporting material on the dryer tube.

5. The method of claim 1, further comprising spraying a mixture of the hygroscopic coating and a solvent on the support material, and then drying the hygroscopic coating.

6. The method of claim 1, further comprising dipping the support material in a mixture of the hygroscopic coating and a solvent, and then drying the hygroscopic coating.

7. The method of claim 1, further comprising:

providing feedback to a controller from a temperature sensor.

8. The method of claim 1 wherein the hygroscopic coating is applied with a coating thickness of about 10% of the a thickness of the support material.

9. A purge and trap concentrator, comprising:

a dryer tube having an inlet that receives a stream of sample gas during a drying interval and that receives a stream of dry gas during a regeneration interval; the dryer tube including a tube wall surrounding an interior passageway between the inlet and an outlet;

a support material disposed in the interior passageway, the support material comprising polymer sorbent and having a support surface area;

a hygroscopic coating disposed on the support surface area, the hygroscopic coating comprising lithium chloride;

a heater providing heat to the hygroscopic coating;

a controller controlling the heater to increase a temperature of the dryer tube to between 100 and 300 degrees centigrade during the regeneration interval and controlling the heater to decrease the temperature of the dryer tube to below 100 degrees centigrade during the drying interval; and a gas metering system providing a regulated flow of dry gas through the interior passageway during the regeneration interval.

10. The purge and trap concentrator of claim 9, wherein the support material comprises fibers.

11. The purge and trap concentrator of claim 10 wherein the fibers are woven to form a fabric.

12. The purge and trap concentrator of claim 9 wherein the support material comprises a mesh.

13. The purge and trap concentrator of claim 9 wherein the dryer tube wall has a surface and the support material is deposited on the surface.

14. The purge and trap concentrator of claim 9 wherein the support material is positioned in the dryer tube by a screen.

15. The purge and trap concentrator of claim 9, further comprising:

a temperature sensor arranged on the dryer tube and providing feedback to the controller.

16. The purge and trap concentrator of claim 9 wherein the hygroscopic coating has a coating thickness of about 10% of a thickness of the support material.

17. A purge and trap concentrator including a first dryer tube and first controller as recited in claim 9, combined with a second dryer tube and second controller, also as recited in claim 9, the first controller providing a drying interval when the second controller is providing a regeneration interval, and the purge and trap concentrator providing the stream of sample gas alternatively to first and second inlets of the first and second dryer tubes, respectively, and the outlets of the first and second dryer tubes alternately couplable to a gas analysis instrument.

* * * * *

UNITED STATES PATENT AND TRADEMARK OFFICE
CERTIFICATE OF CORRECTION

| | |
|---|---|
| PATENT NO. | : 6,929,678 B2 |
| APPLICATION NO. | : 10/440661 |
| DATED | : August 16, 2005 |
| INVENTOR(S) | : Hartlein |

It is certified that error appears in the above-identified patent and that said Letters Patent is hereby corrected as shown below:

Column 1, line 32, delete "cake up" and replace therewith --"cake up"--.

Column 7, line 43, delete "on lines" and replace therewith --on line--.

Column 8, line 63, delete "the a thickness" and replace therewith --a thickness--.

Signed and Sealed this

Third Day of April, 2007

JON W. DUDAS
*Director of the United States Patent and Trademark Office*